United States Patent
Kuriyama et al.

(10) Patent No.: US 10,302,618 B2
(45) Date of Patent: May 28, 2019

(54) METHOD FOR DIAGNOSING OIL-FILLED ELECTRICAL APPARATUS

(71) Applicant: MITSUBISHI ELECTRIC CORPORATION, Chiyoda-ku, Tokyo (JP)

(72) Inventors: Ryota Kuriyama, Tokyo (JP); Fukutaro Kato, Tokyo (JP); Ryuichi Nishiura, Tokyo (JP); Satoru Toyama, Tokyo (JP); Kota Mizuno, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 248 days.

(21) Appl. No.: 15/326,661

(22) PCT Filed: Aug. 27, 2014

(86) PCT No.: PCT/JP2014/072399
§ 371 (c)(1),
(2) Date: Jan. 17, 2017

(87) PCT Pub. No.: WO2016/030984
PCT Pub. Date: Mar. 3, 2016

(65) Prior Publication Data
US 2017/0199170 A1    Jul. 13, 2017

(51) Int. Cl.
*G01N 30/02*     (2006.01)
*G01N 30/72*     (2006.01)
(Continued)

(52) U.S. Cl.
CPC ......... *G01N 33/2841* (2013.01); *G01N 30/02* (2013.01); *G01N 30/7206* (2013.01);
(Continued)

(58) Field of Classification Search
CPC .................. G01N 33/2841; G01N 33/2835
See application file for complete search history.

(56) References Cited

U.S. PATENT DOCUMENTS 4,402,211 A     9/1983 Sugawara et al.

FOREIGN PATENT DOCUMENTS

JP     57-001203 A     1/1982
JP     5-052787 A      3/1993
(Continued)

OTHER PUBLICATIONS

Lewand, Lance R., et al. "Case Studies Involving Insulating Liquids and Materials From the Doble Materials Laboratories" 77th Annual International Doble Client Conference, 2010. (Year: 2010).*

(Continued)

*Primary Examiner* — Paul M. West
(74) *Attorney, Agent, or Firm* — Buchanan Ingersoll & Rooney PC

(57) ABSTRACT

The method for diagnosing the oil-filled electrical apparatus in the present invention is a method for diagnosing whether or not discharge has occurred inside the oil-filled electrical apparatus. The diagnosing method includes: an in-oil gases analyzing step of analyzing hydrogen gas and a gas selected from the group consisting of methane, ethane, ethylene, acetylene, hydrocarbon having a carbon number of 3 or 4, carbon monoxide, carbon dioxide, oxygen, and nitrogen, contained in an insulating oil used inside the oil-filled electrical apparatus; a step of analyzing a causative substance serving as a cause of generation of hydrogen in the insulating oil irrespective of whether or not the discharge has occurred; and a step of diagnosing whether or not the discharge has occurred based on an analysis result of the in-oil gases analyzing step and an analysis result of the step of analyzing the causative substance.

5 Claims, 1 Drawing Sheet

(51) Int. Cl.
*G01N 33/28* (2006.01)
*H01F 27/00* (2006.01)

(52) U.S. Cl.
CPC ......... *G01N 33/2835* (2013.01); *H01F 27/00* (2013.01); *G01N 2030/027* (2013.01)

(56) References Cited

FOREIGN PATENT DOCUMENTS

| JP | 9-072892 A | 3/1997 |
|---|---|---|
| JP | 3081717 U | 11/2001 |
| JP | 2004-200348 A | 7/2004 |
| JP | 2008-042130 A | 2/2008 |
| JP | 2013-015409 A | 1/2013 |

OTHER PUBLICATIONS

International Search Report (PCT/ISA/210) dated Oct. 7, 2014, by the Japanese Patent Office as the International Searching Authority for International Application No. PCT/JP2014/072399.
Written Opinion (PCT/ISA/237) dated Oct. 7, 2014, by the Japanese Patent Office as the International Searching Authority for International Application No. PCT/JP2014/072399.
Decision to Grant Patent dated Jan. 27, 2015 in Application No. 2014-553004, 3 pages (with English language translation, pp. 1-3).
Zhongdong Wang et al., "Gas Generation in Natural Ester and Mineral Oil Under Partial Discharge and Sparking Faults", IEEE Electrical Insulation Magazine, Sep./Oct. 2013, vol. 29, No. 5, pp. 62-70.
CIGRE WG A2-32, "Copper Sulphide in Transformer Insulation", Final Report, Brochure 378, 2009, pp. 1-35.

\* cited by examiner

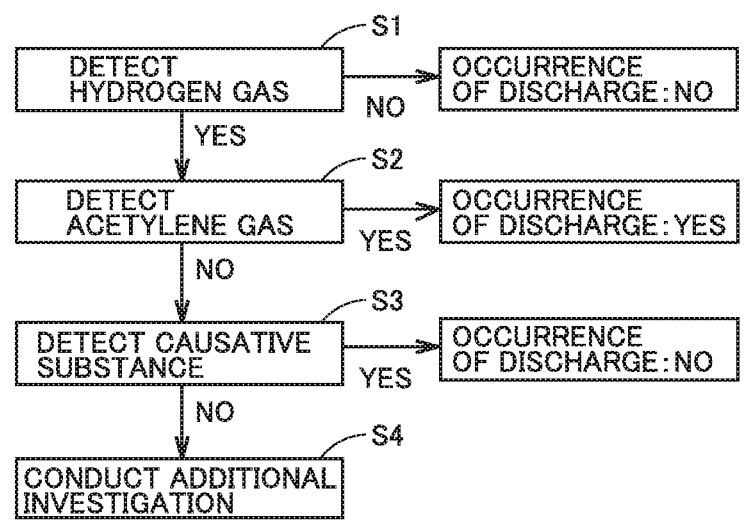

METHOD FOR DIAGNOSING OIL-FILLED ELECTRICAL APPARATUS

TECHNICAL FIELD

The present invention relates to a method for diagnosing an oil-filled electrical apparatus, and relates to, for example, a method for diagnosing an abnormality caused by discharge inside an oil-filled electrical apparatus such as an oil-filled transformer.

BACKGROUND ART

In order to diagnose an abnormality inside an oil-filled electrical apparatus, analysis of a gas in an oil, by which a diagnosis can be made without stopping the apparatus, is used at home and abroad (for example, PTD 1: Japanese Patent Laying-Open No. 2004-200348, and NPD 1: Z. Wang, X. Wang, X. Yi and S. Li, "Gas Generation in Natural Ester and Mineral Oil Under Partial Discharge and Sparking Faults", IEEE Electrical Insulation Magazine, Vol. 29, No. 5, pp. 62-70, 2013). In order to determine whether or not there is an internal abnormality and to determine the type (cause) thereof, types of gas components contained in an oil, concentrations thereof in the oil, a concentration ratio therebetween, and the like are used as parameters.

As a method for diagnosing whether or not there is an abnormality caused by discharge (discharge abnormality), which is a type of internal abnormality, diagnostic methods using hydrogen gas and acetylene gas as parameters are known. Compared with acetylene gas, hydrogen gas is generated at a lower temperature and in a larger amount. Thus, the diagnostic method using hydrogen gas as a parameter can diagnose a discharge abnormality earlier than a diagnostic method not using hydrogen gas as a parameter.

CITATION LIST

Patent Document

PTD 1: Japanese Patent Laying-Open No. 2004-200348

Non Patent Document

NPD 1: Z. Wang, X. Wang, X. Yi and S. Li, "Gas Generation in Natural Ester and Mineral Oil Under Partial Discharge and Sparking Faults", IEEE Electrical Insulation Magazine, Vol. 29, No. 5, pp. 62-70, 2013
NPD 2: "Copper sulphide in transformer insulation", Final Report Brochure 378, 2009

SUMMARY OF INVENTION

Technical Problem

However, hydrogen gas may be generated due to a cause other than a discharge abnormality in an oil-filled electrical apparatus. For example, there is known a phenomenon that, when Irgamet (registered trademark) 39[N,N-bis(2-ethylhexyl)-(4 or 5)-methyl-1H-benzotriazol-1-methylamine], which is a copper sulfide generation inhibitor, is added to an insulating oil, hydrogen gas is generated in the insulating oil (see, for example, NPD 2: CIGRE WG A2-32, "Copper sulphide in transformer insulation," Final Report Brochure 378, 2009).

In addition, it has been found through studies conducted by the present inventors that, for example, when an adhesive used to bond coil copper wires contains boron trifluoride, the boron trifluoride may react with coil copper and thereby hydrogen gas may be generated.

Taking these phenomena into consideration, there is a possibility that, in the case of diagnosing a discharge abnormality in an oil-filled electrical apparatus using at least hydrogen gas as a parameter, it may be determined that there is a discharge abnormality in the oil-filled electrical apparatus even when hydrogen gas is detected due to a cause other than a discharge abnormality, which may lead to an incorrect diagnosis.

The present invention has been made in view of the aforementioned problem, and one object of the present invention is to provide a method for diagnosing an oil-filled electrical apparatus capable of diagnosing whether or not discharge has occurred inside the oil-filled electrical apparatus with higher accuracy than before.

Solution to Problem

A method for diagnosing an oil-filled electrical apparatus in the present invention is a method for diagnosing whether or not discharge has occurred inside the oil-filled electrical apparatus. The method for diagnosing the oil-filled electrical apparatus in the present invention is characterized by including: an in-oil gases analyzing step of analyzing hydrogen gas and at least one gas selected from the group consisting of methane, ethane, ethylene, acetylene, hydrocarbon having a carbon number of 3 or 4, carbon monoxide, carbon dioxide, oxygen, and nitrogen, contained in an insulating oil used inside the oil-filled electrical apparatus; a step of analyzing a causative substance serving as a cause of generation of hydrogen in the insulating oil irrespective of whether or not the discharge has occurred; and a step of diagnosing whether or not the discharge has occurred based on an analysis result of the in-oil gases analyzing step and an analysis result of the step of analyzing the causative substance.

Advantageous Effects of Invention

According to the present invention, a method for diagnosing an oil-filled electrical apparatus capable of diagnosing whether or not discharge has occurred inside the oil-filled electrical apparatus with higher accuracy than before can be provided.

BRIEF DESCRIPTION OF DRAWINGS

FIG. 1 is a flowchart for illustrating one example of a diagnosing step in a method for diagnosing an oil-filled electrical apparatus in one embodiment of the present invention.

DESCRIPTION OF EMBODIMENTS

A method for diagnosing an oil-filled electrical apparatus in the present embodiment is a method for diagnosing whether or not discharge has occurred inside the oil-filled electrical apparatus. The method for diagnosing the oil-filled electrical apparatus in the present embodiment includes at least an in-oil gases analyzing step, a causative substance analyzing step, and a diagnosing step described below.

(In-Oil Gases Analyzing Step)

In this step, hydrogen gas and at least one gas selected from the group consisting of methane, ethane, ethylene, acetylene, hydrocarbon having a carbon number of 3 or 4, carbon monoxide, carbon dioxide, oxygen, and nitrogen, contained in an insulating oil used inside the oil-filled electrical apparatus are analyzed. Examples of the hydrocarbon having a carbon number of 3 or 4 include propane, propylene, and butane. Of these gases, in particular, acetylene, hydrogen, methane, ethane, ethylene, and carbon monoxide are preferably analyzed.

As a method for analyzing these gas components in the insulating oil, any known in-oil gases analyzing method can be used. For example, a method disclosed in PTD 1 or NPD 1 described above can be used. The device used for the analysis is not particularly limited, and any known gas analyzer can be used. For example, a gas chromatograph or a gas chromatograph mass spectrometer (GC-MS) can be used.

It should be noted that this step can be performed without stopping operation of the oil-filled electrical apparatus, by analyzing the insulating oil taken from the oil-filled electrical apparatus in operation.

(Causative Substance Analyzing Step)

In this step, a causative substance serving as a cause of generation of hydrogen in the insulating oil irrespective of whether or not the discharge has occurred is analyzed.

In the method for diagnosing the oil-filled electrical apparatus in the present embodiment, the causative substance serving as a cause of generation of hydrogen in the insulating oil irrespective of whether or not the discharge has occurred is preferably at least one selected from boron trifluoride and a benzotriazole compound.

When at least the boron trifluoride is analyzed in the step of analyzing the causative substance described above, the boron trifluoride is a gas component, and thus can be analyzed using any known method for measuring a gas component in an oil.

Preferably, the boron trifluoride is analyzed by a gas analysis method including a step of heating the insulating oil, and extracting and condensing the boron trifluoride dissolved in the insulating oil from the heated insulating oil by bubbling using an inert gas, because the boron trifluoride dissolved in the insulating oil is a minor component.

It should be noted that, as such a gas analysis method, for example, an analysis method using a gas analyzer disclosed in Japanese Patent Laying-Open No. 09-72892 can be used.

Further, the device used for the analysis is not particularly limited, and any known gas analyzer can be used. For example, a gas chromatograph or a gas chromatograph mass spectrometer (GC-MS) can be used.

When at least the benzotriazole compound is measured in the step of analyzing the causative substance described above, the benzotriazole compound is a liquid component, and thus can be analyzed using any known method for measuring a liquid component in an oil.

The benzotriazole compound can be analyzed, for example, by liquid chromatography such as high-performance liquid chromatography. It should be noted that, as a device used for the analysis, for example, a liquid chromatograph such as a high-performance liquid chromatograph can be used.

The benzotriazole compound is not particularly limited as long as it can serve as a cause of generation of hydrogen in the insulating oil irrespective of whether or not the discharge has occurred. For example, Irgamet (registered trademark) 39 [N,N-bis(2-ethylhexyl)-(4 or 5)-methyl-1H-benzotriazol-1-methylamine] can be used.

It should be noted that this step can also be performed without stopping operation of the oil-filled electrical apparatus, by analyzing the insulating oil taken from the oil-filled electrical apparatus in operation.

(Diagnosing Step)

In this step, whether or not the discharge has occurred is diagnosed based on an analysis result of the in-oil gases analyzing step and an analysis result of the causative substance analyzing step. It should be noted that whether or not the discharge has occurred is comprehensively diagnosed based on the analysis result of the in-oil gases analyzing step and the analysis result of the causative substance analyzing step.

Hereinafter, one example of the diagnosing step in the method for diagnosing the oil-filled electrical apparatus in the present embodiment will be specifically described with reference to the drawing. It should be noted that a description will be given herein of a case where acetylene gas is analyzed as the at least one gas selected from the group consisting of methane, ethane, ethylene, acetylene, hydrocarbon having a carbon number of 3 or 4, carbon monoxide, carbon dioxide, oxygen, and nitrogen.

Referring to FIG. 1, first, in step 1 (S1), it is checked whether or not the hydrogen gas has been detected in the in-oil gases analyzing step described above. When the hydrogen gas has not been detected, it is diagnosed that there is a high possibility that no discharge has occurred inside the oil-filled electrical apparatus. On the other hand, when the hydrogen gas has been detected, the process proceeds to step 2 (S2).

Next, when the process proceeds to step 2 (S2), it is checked whether or not the acetylene gas has been detected in the in-oil gases analyzing step described above. When the acetylene gas has been detected, it is considered that the cause of generation of the hydrogen gas is discharge, and thus it is diagnosed that there is a high possibility that the discharge has occurred inside the oil-filled electrical apparatus. On the other hand, when the acetylene gas has not been detected, there is a possibility that the cause of generation of the hydrogen gas may not be discharge, and thus the process proceeds to subsequent step 3 (S3).

Next, when the process proceeds to step 3 (S3), it is checked whether or not the causative substance has been detected in the causative substance analyzing step described above. When the causative substance has been detected, it is considered that there is a high possibility that the cause of generation of the hydrogen gas is not discharge, and thus it is diagnosed that there is a high possibility that no discharge has occurred inside the oil-filled electrical apparatus.

It should be noted that, when the boron trifluoride has been detected as the causative substance, it is considered that there is a high possibility that the cause of generation of the hydrogen gas is a boron trifluoride-containing adhesive used for the oil-filled electrical apparatus. Further, when Irgamet 39 has been detected as the causative substance, it is considered that there is a high possibility that the cause of generation of the hydrogen gas is Irgamet 39 added as a copper sulfide generation inhibitor.

On the other hand, when the causative substance has not been detected, it is not possible to determine whether or not the cause of generation of the hydrogen gas is discharge, and thus the process proceeds to subsequent step 4 (S4).

Next, when the process proceeds to step 4 (S4), an additional investigation for determining whether or not the cause of generation of the hydrogen gas is discharge is conducted.

As the additional investigation, for example, it is checked whether or not a boron trifluoride-containing adhesive is used for the oil-filled electrical apparatus. This check can be made for example by checking the specifications of the oil-filled electrical apparatus.

When it is found that a boron trifluoride-containing adhesive is used, the drying temperature in the process of manufacturing the oil-filled electrical apparatus is then checked to investigate the possibility that hydrogen generated by a reaction between the boron trifluoride in the adhesive and a coil has dissolved into the insulating oil. This check can be made for example by checking an operation history in the manufacturing process.

When the drying temperature is higher than or equal to the curing temperature of the adhesive, it is considered to be unlikely that the hydrogen gas has dissolved from the adhesive. In this case, a diagnosis that the discharge has occurred can be made based on the detection of the hydrogen gas in the in-oil gases analyzing step.

As another additional investigation, for example, it is checked whether or not there is a history that Irgamet 39 (copper sulfide generation inhibitor) has been added into the insulating oil. This check can be made for example by checking a storage management record of the oil-filled electrical apparatus.

When it is found that there is no history that Irgamet 39 (copper sulfide generation inhibitor) has been added, it is considered to be unlikely that the hydrogen gas has been generated by the addition of Irgamet 39. In this case, a diagnosis that the discharge has occurred can be made based on the detection of the hydrogen gas in the in-oil gases analyzing step.

It should be noted that, when it is considered that Irgamet 39 has been exhausted based on the time at which Irgamet 39 was added and the added amount thereof, the insulating oil may be degassed to remove the hydrogen gas in the insulating oil. Thereafter, the hydrogen gas in the insulating oil is monitored. When the hydrogen gas is also detected in the degassed insulating oil, it can be diagnosed that there is a high possibility that the discharge has occurred.

With the method for diagnosing the oil-filled electrical apparatus in the present embodiment, whether or not the discharge has occurred inside the oil-filled electrical apparatus can be diagnosed with higher accuracy than before.

It should be understood that the embodiment disclosed herein is illustrative and non-restrictive in every respect. The scope of the present invention is defined by the scope of the claims, rather than the description above, and is intended to include any modifications within the scope and meaning equivalent to the scope of the claims.

The invention claimed is:

1. A method for diagnosing whether or not discharge has occurred inside an oil-filled electrical apparatus, comprising:
    an in-oil gases analyzing step of analyzing hydrogen gas and at least one gas selected from the group consisting of methane, ethane, ethylene, acetylene, hydrocarbon having a carbon number of 3 or 4, carbon monoxide, carbon dioxide, oxygen, and nitrogen, contained in an insulating oil used inside the oil-filled electrical apparatus;
    a step of analyzing a causative substance serving as a cause of generation of the hydrogen in the insulating oil irrespective of whether or not the discharge has occurred; and
    a step of diagnosing whether or not the discharge has occurred based on an analysis result of the in-oil gases analyzing step and an analysis result of the step of analyzing the causative substance,
    wherein the causative substance is boron trifluoride or a benzotriazole compound.

2. The method for diagnosing the oil-filled electrical apparatus according to claim 1, wherein, in the step of analyzing the causative substance, at least the boron trifluoride is analyzed.

3. The method for diagnosing the oil-filled electrical apparatus according to claim 2, wherein the boron trifluoride is analyzed by a gas analysis method including a step of heating the insulating oil, and extracting and condensing the boron trifluoride dissolved in the insulating oil from the heated insulating oil by bubbling using an inert gas.

4. The method for diagnosing the oil-filled electrical apparatus according to claim 1, wherein, in the step of analyzing the causative substance, at least the benzotriazole compound is measured.

5. The method for diagnosing the oil-filled electrical apparatus according to claim 4, wherein the benzotriazole compound is analyzed by high-performance liquid chromatography.

* * * * *